Figure 1A:
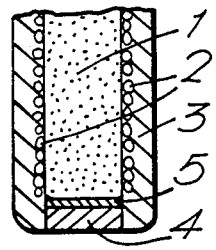

United States Patent [19]

Forrest et al.

[11] Patent Number: 4,978,610
[45] Date of Patent: Dec. 18, 1990

[54] METHOD OF ASSAY EMPLOYING A MAGNETIC ELECTRODE

[76] Inventors: Gordon C. Forrest, Braemore, High Park Avenue, East Horsley, Surrey KT24 5DP; Simon J. Rattle, 52 Mabel Street, Woking, Surrey GU21, 1 NW; Grenville A. Robinson, 23 Burnham Way, Ealing, London, W13 9YE; Hugh A. O. Hill, 9 Clover Close, Oxford, all of England

[21] Appl. No.: 76,265

[22] Filed: Jul. 23, 1987

Related U.S. Application Data

[63] Continuation of Ser. No. 753,155, Jul. 9, 1985, abandoned.

[30] Foreign Application Priority Data

Jul. 10, 1984 [GB] United Kingdom ............... 8417538
Jan. 25, 1985 [GB] United Kingdom ............... 8501925
Apr. 4, 1985 [GB] United Kingdom ............... 8508861

[51] Int. Cl.$^5$ .................... C12Q 1/25; G01N 33/53
[52] U.S. Cl. ............................ 435/7; 204/153.1; 204/400; 204/403; 204/DIG. 5; 435/14; 435/25; 435/817; 436/526; 436/806; 436/536; 436/501
[58] Field of Search ............ 435/7, 817; 436/526; 436/806; 204/1 T, 400, 403

[56] References Cited

U.S. PATENT DOCUMENTS 4,219,335 8/1980 Ebersole ............................ 436/526
4,751,053 6/1988 Dodin et al. ...................... 436/526

OTHER PUBLICATIONS

"Magnetic Enzyme Membranes as Active Elements of Electrochemical Sensors Specific Amino Acid Enzyme Electrodes*", by C. Calvot et al., FEBS Letters, vol. 59, No. 2, Nov. 1975, pp. 258–262.

"Magnetic Enzyme Membranes as Active Elements of Electrochemical Sensors, Lactose, Saccharose, Maltrose Bienzyme Electrodes*", by M. Cordonnier et al., FEBS Letters, vol. 59, No. 2, Nov. 1975, pp. 263–267.

Primary Examiner—Sam Rosen
Attorney, Agent, or Firm—Ostrolenk, Faber, Gerb & Soffen

[57] ABSTRACT

In its broadest aspect, the present invention provides a method of effecting an electrochemical specific-binding assay of a ligand, either qualitatively or quantitatively, in an apparatus comprising at leasts one electrode, in which method a labelled component of the assay medium is, at least in part, magnetically held in the vicinity of the electrode. The electrochemical assay method may include a separation step, whereby bound label may be separated from free label in the assay medium. Preferably the electrochemical assay method will include the step of determining a perturbation in an electrochemical characteristic of components of the assay medium associated with a ligand complexing reaction.

Such an assay method is applicable to, for example, antibodies and antigens and suitable labels include redox centers, enzyme labels in the presence of an electron-transfer mediator and electron-transfer mediator labels in the presence of an electron donor or acceptor.

14 Claims, 6 Drawing Sheets

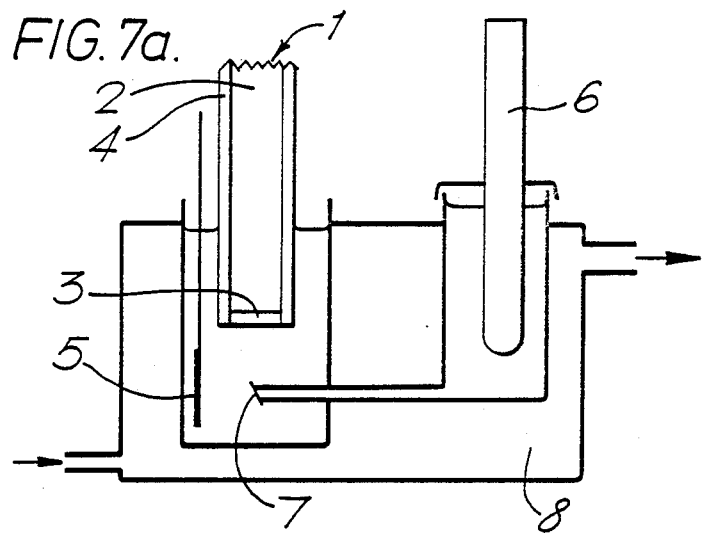
FIG. 7a.
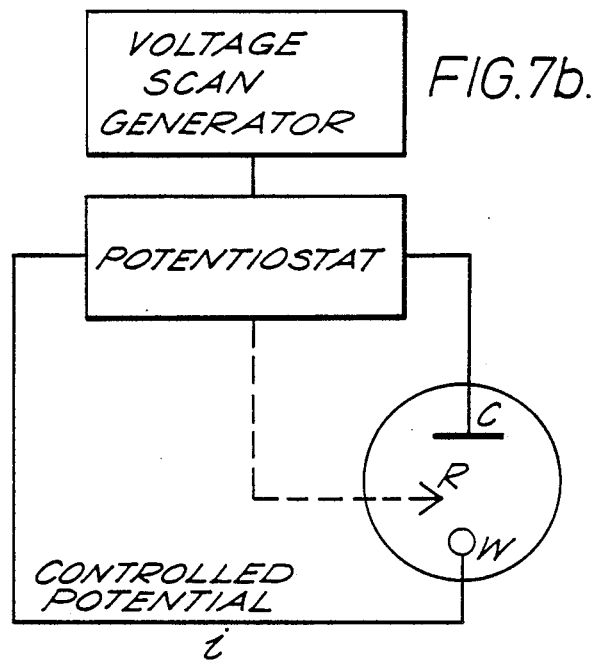
FIG. 7b.
FIG. 10.

METHOD OF ASSAY EMPLOYING A MAGNETIC ELECTRODE

This is a continuation of application Ser. No. 753,155, filed July 9, 1985, and now abandoned.

The present invention relates to methods of assaying one of a pair of specific binding partners, and in particular to methods employing magnetic electrodes.

In our copending European Patent Application Nos. 84307300.8, 85300508.0, 85301497.5 and 85303367.8 entitled "Methods of Assay", we describe new methods of specific-binding assays for quantitatively or qualitatively assaying ligands. For the avoidance of doubt, the terminology relating to the binding partners used in our prior applications will be applied hereinafter, that is to say, "ligand" refers to the species under assay, "specific binding partner" refers to a species to which the ligand will bind specifically, and "ligand analogue" refers to a species also capable of complexing with the specific binding partner and including inter alia within its scope a known quantity of the ligand.

The components of the assay medium in these assay methods comprise an electroactively labelled reagent, which label, either alone or in cooperation with an electron-transfer mediator or an electron donor or acceptor, causes a transfer of electrons to or from an electrode. In these methods, the assay is determined by measuring a perturbation in an electrochemical characteristic of the components, associated with complex formation. Measurements are taken at the working electrode of, typically, a three-electrode apparatus and the assay is calculated by reference to calibration data obtained under similar conditions with known amounts of reagents.

A variety of electrochemical methods exploiting any two of the three parameters potential (E), current (i) and time (t) may be used to measure electrochemical characteristics of the components. For example, electrochemical measurements can be made using differential pulse voltammetry, cyclic voltammetry or square-wave voltammetry. It is not necessary for a full voltammogram to be determined; it may be sufficient, for example, for an appropriate poised potential to be selected and readings of current taken at that point.

Methods are also described in which a rate of perturbation of the electrochemical characteristic (rather than absolute perturbation) associated with complex formation is determined. For example, in a competitive assay in which the ligand and a labelled ligand analogue compete for complexing with the specific binding partner, the rate of perturbation (e.g. the initial rate) is related to the concentration of ligand present and from a calibration plot of the rate of perturbation v concentration of ligand present, the ligand assay can be readily determined.

Modifications of these methods are also described in the above-mentioned applications wherein a perturbation is artificially generated or enhanced by displacing the complexed or uncomplexed material relative to the electrode. This may be achieved, for example, by complexing the complexed or uncomplexed material with a species to which it will bind specifically, said species being coupled to a solid support, with subsequent displacement of the support and coupled molecules.

It may also be necessary completely to separate the complexed and uncomplexed material before measuring the perturbation. Thus, for example, in the heterogeneous techniques described in our European Patent Application No. 85300508.0, or in the competitive and sandwich techniques as described in our European Patent Application No. 85303367.8, such a separation step may be necessary.

The new methods described in the above applications possess significant advantages over conventional methods of assay (e.g. radioimmunoassay or enzyme immunoassay). In particular, they are generally simpler than conventional methods and avoid the use of hazardous or legally-restricted reagents, while preserving at least the same level of sensitivity and specificity as the conventional methods.

However, in these new methods, unless the poised potential technique, which employs a stirred system, is used when taking measurements, the sensitivity and specificity will generally be dependent on the mobility of the electroactive species and their ability to diffuse to the electrode. This may give rise to some inaccuracy, for example, if some of the electroactive species is entrapped in the complexed material with consequent reduction in mobility, or if access of the electroactive species to the electrode is prevented by the shielding effect of the complex phase.

We have now found that, by enabling a labelled component of the assay medium to be at least in part magnetically held near an electrode, the sensitivity and specificity of the methods may be improved, and any separation and/or displacement steps in the methods may be simplified.

Thus, in its broadest aspect, the present invention provides a method of effecting an electrochemical specific-binding assay of a ligand, either qualitatively or quantitatively, in an apparatus comprising at least one electrode, in which method a labelled component of the assay medium is, at least in part, magnetically held in the vicinity of the electrode.

The electrochemical assay method may include a separation step, whereby bound label may be separated from free label in the assay medium.

Preferably the electrochemical assay method will include the step of determining a perturbation in an electrochemical characteristic of components of the assay medium associated with a ligand complexing reaction.

It will be appreciated that the method of the present invention is applicable to electroactive labels (i.e. labels which, either alone or in cooperation with an electron-transfer mediator or electron donor or acceptor, may be monitored by electrical measurement at an electrode), and inter alia to any of the types of labels described in our prior copending European patent applications mentioned above, i.e. "redox centres", enzymes and electron-transfer mediators.

Redox centres require no cooperating electron-transfer mediator or electron donor or acceptor. A preferred redox centre is the organo-metallic 'sandwich' compound ferrocene (bis-5-cyclopentadienyl iron (II)) or a derivative thereof. These compounds are desirable for this purpose because they are relatively cheap, non-toxic, water soluble and provide an easily electrochemically reversible system which in its reduced $Fe^{II}$ state is not susceptible to oxidation by oxygen in the atmosphere. Incorporation of ferrocene into the molecular structure of an antibody or antigen has been found to cause no immunological change in the antibody or antigen. Examples of suitable ferrocene derivatives include functionalised derivatives, polymeric forms ('polyferrocenes') such as (ferrocene)₄ and 'boron tetraferrocene' (B(ferrocene)₄).

Examples of other redox centres which may be employed include nitroxides, viologens, derivatives of phenazine methosulphate and phenazine ethosulphate, metal carbonyls (such as, for example, chromium carbonyl or molybdenum carbonyl) and their derivatives, and transition metal Schiff's base derivatives.

Modification of the label may be necessary to permit successful binding to e.g. reagents. The redox potential of ferrocene is +422 mV vs NHE. By introducing functional groups onto the ring system, this figure can be varied between +300 and +650 mV. Moreover, the water-solubility of carboxyl-substituted ferrocene is greater then that of the parent compound (see, for example, R. Szentrimay, 1977, Amer. Chem. Soc. Symposium Series, 38, 154).

Thus, for example, in the case of ferrocene, modification may be achieved by providing one or both of the cyclopentadienyl groups with one or more side chains, e.g. of the formula

—CHO

—(CH₂)ₙCOOH or

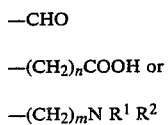

wherein n and m may be e.g. from 0 to 6 and $R^1$ and $R^2$, which may be the same or different, each represents hydrogen or an alkyl group containing from 1 to 4 carbon atoms (e.g. methyl). Additional functional groups may be incorporated into the side chain, typically those groups used in the chemical modification of proteins, for example mercuric chloride, precursors of nitrenes and carbenes, diazo or iodide group. The terminal —COOH or —NH₂ groups are then available to interact with suitable sites. The length of the side chain (i.e. the value of n or m) will depend on the structure of the antibody or antigen to which the ferrocene is to be bound. Similar functionalisation may be desirable when redox centres other than ferrocene are used.

Appropriate enzyme labels will require the presence of an electron-transfer mediator. The term "enzyme" used herein includes both true enzymes and apoenzymes which may become activated in the presence of a cofactor. The site of attachment to the reagent will generally be remote from the active site of the enzyme so that the enzyme activity is not impaired. Preferred enzymes are the so-called oxidoreductases, particularly, but not exclusively, flavo- and quino-protein enzymes, e.g. glucose oxidase, glucose dehydrogenase or methanol dehydrogenase. As an apoenzyme, for example, apoglucose oxidase may be used with flavin adenine dinucleotide (FAD) as a cofactor.

The enzyme may be attached to reagents by any of the conventional methods for coupling, for example, employing covalent or non-covalent bonding using bifunctional reagents such as glutaraldehyde, periodate, N,N'-o-phenylene-dimaleimide, m-maleimido-benzoyl-N-hydroxysuccinimide ester, succinic anhydride, a mixed anhydride, or a carbodiimide. Alternatively, cross-linking or the formation of, for example, an avidin/biotin or protein A/IgG complex may be used.

The electron transfer mediator can accept electrons from the enzyme and donate them to the electrode (during substrate oxidation) or can accept electrons from the electrode and donate them to the enzyme (during substrate reduction).

The mediator may, for example, be selected from the following:

(i) a polyviologen such as, for example, a compound of formula

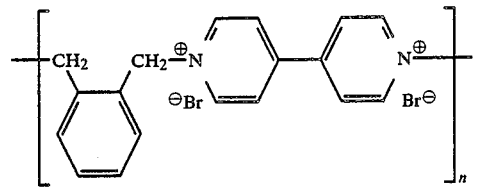

and derivatives thereof, e.g. side-chain alkyl derivatives, the preparation of which is described in Polymer Letters 9 pp 289–295 (1971).

(ii) a low molecular weight compound selected from chloranils, fluoranils and bromanils (e.g. o-chloranil), (iii) ferrocene or a derivative thereof [including e.g. functionalised derivatives such as ferrocene monocarboxylic acid (FMCA), polymeric forms ('polyferrocenes') such as (ferrocene)₄ or polyvinyl ferrocene and 'boron tetraferrocene' (B(ferrocene)₄)], (iv) compounds of biological origin possessing suitable enzyme compatability, e.g. Vitamin K.

(v) N,N,N',N'-tetramethyl-4-phenylenediamine, and (vi) derivatives of phenazine methosulphate or phenazine ethosulphate.

Mediators may interact with the enzyme at a site remote from or near to the active site for the substrate reaction, and remote from or near to the site of attachment to the reagent. Proximity of the site of enzyme-mediator interaction to the site of attachment of the reagents can result in prevention of electron transfer between the enzyme and the mediator on formation of the complex between the ligand or ligand analogue and the specific binding partner, permitting a homogeneous assay method.

The preferred electron transfer mediators are ferrocene and functionalised derivates thereof. Functionalisation may be analagous to that described above in relation to redox centres. Similar functionalisation may be desirable when mediators other than ferrocene are used.

Such mediators may also be labels and will then be used in cooperation with an electron donor or acceptor (e.g. an oxidoreductase enzyme of the type described above). In addition, a cofactor of an apoenzyme may be used as a label, the cofactor interacting with the apoenzyme in the normal way.

Mediators which cooperate with electron-sources or acceptors other than enzymes may also be employed as labels. Thus, for example, apomorphine, substituted catechols (such as 1-amino-2-(3,4-dihydroxyphenyl)-ethane or 1-amino-2-(3,4,5-trihydroxyphenyl)-ethane) or aminophenols (such as p-aminophenol or 1-amino-2-(2-amino-4,5-dihydroxyphenyl)-ethane) may be used, with ascorbate as an electron-source, or quinones (such as o-quinones) may be used, with dihydronicotinamide adenosine diphosphate (NADH) as an electron-source.

However, the present invention is not limited to these electroactive labels, but is equally applicable to other electrochemical specific-binding assays in which the label used is, for example a chemiluminescent species e.g. luminol.

Preferably, the labelled component of the assay medium will be retained in the vicinity of the working electrode by immobilising at least some of the labelled component on a magnetic support (e.g. in the form of particles or beads) and employing a magnetic working electrode. Suitable methods for immobilising labelled components on magnetic supports are described below.

The term "magnetic" and like expressions used herein shall be taken to include permanently and temporarily magnetic materials, and materials which will respond to the presence of a magnetic field although not themselves magnetised.

Thus, for example, magnetic supports (e.g. in the form of particles or beads) may be composed of ferromagnetic or paramagnetic materials such as metals (e.g. iron, nickel or cobalt), metal alloys (e.g. magnetic alloys of aluminium, nickel, cobalt and copper), metal oxides (e.g. $Fe_3O_4$, $\gamma$-$Fe_2O_3$, $CrO_2$, $CoO$, $NiO$ or $Mn_2O_3$), magnetoplumbites or solid solutions (e.g. solid solutions of magnetite with ferric oxide). The preferred material for magnetic supports is magnetite ($Fe_3O_4$) or haematite ($\gamma$-$Fe_2O_3$).

If desired, the nature of the magnetic material may be altered to suit the circumstances of the assay. Thus, for example, particles may be provided with a non-magnetic polymeric matrix or coating (e.g. of glass or of synthetic or naturally-occurring polymeric materials such as, for example, proteins, cellulose derivatives, agarose or polystyrene) to reduce their overall density and/or to facilitate immobilisation of reagents and/or to passivate the particles so that they show no significant electrochemistry in the potential range of interest (typically 0 to +550 mV).

The particles may be colloidal or non-colloidal. The size of the particles may, for example be in the range 10 to 800 nm, although, if desired, may be above or below this range. The specific gravity of such particles will typically be up to 8, e.g. from 2 to 6. Colloidal particles have the advantage that they will not appreciably sediment out under the effects of gravity within the time taken to perform the assay (typically up to 1 or 2 hours). Colloidal magnetic particles of the type described in our prior copending British Patent Application No. 8500092 may for example be used.

Where required the labelled component may be immobilised directly on the magnetic support, or may be immobilised via one or more other 'spacer' molecules, including partners in specific binding interactions. Direct immobilisation may be via a suitable functional group on the label or may be via the molecular structure of the reagent itself. Immobilisation of reagents may generally be achieved by conventional techniques such as, for example, adsorption, covalent bonding or cross-linking, or a combination of these techniques, e.g. adsorption of a chemical with one or more functional groups followed by covalent bonding or cross-linking of the reagent. Alternatively, substantially nonchemical means may be employed. Suitable immobilisation techniques are known in the art, for example those described in Chapter 4 of "Immobilised Enzymes in Analytical and Clinical Chemistry", ed. Carr P. W. and Bowers L. D. (Wiley, New York, (1980)).

A suitable magnetic electrode may comprise a permanent magnet (e.g. of ferrite) or a temporary magnet such as an electromagnet (e.g. of mild steel) or a magnetisable material (e.g. steel) which may be magnetised by contacting the electrode with a permanent magnet. An electromagnetic electrode is generally desirable since the strength of attraction of the magnetic support may more readily be controlled. For example, it is possible that the sensitivity of the assays (particularly those assays in which a redox active reagent label is employed, e.g. assays of the type described in European Patent Application No. 84307300.8) may be improved by pulsing the electromagnetic field between the "on" and "off" states, to enable fresh electroactive species to reach the electrode surface.

However, a permanently magnetic electrode may be cheaper and easier to construct than an electromagnetic one, although it may not be so versatile or controllable and may have to be introduced into the assay medium after the complexing reaction has gone to equilibrium.

The core of the electrode will conveniently be of magnetic material, with the working surface at which electrical measurements may be taken being of an electrically conductive material such as, for example, carbon (preferably graphite), silver, gold or platinum. If desired, the working surface of the electrode may itself be magnetic, e.g. of ferrite.

The nature of the working surface is usually important; if metallic, it can be roughened or chemically modified—if carbon, it can be previously heat-treated in an oven with oxygen excess.

According to a further feature of the present invention, therefore, there is provided a magnetic electrode for use in the methods of assay herein described. Preferably, the electrode will be the working electrode at which electrical measurements can be taken.

Figure 1B:
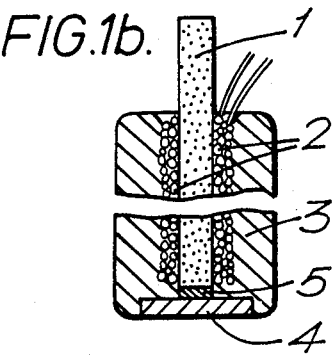
Figure 1C:
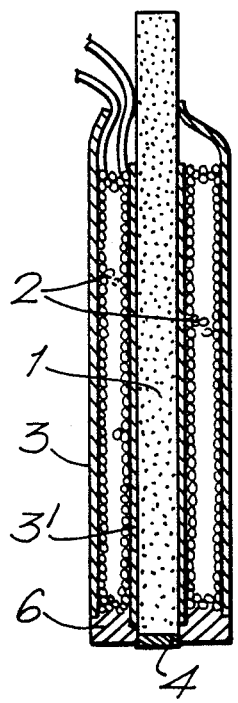
Figure 2:
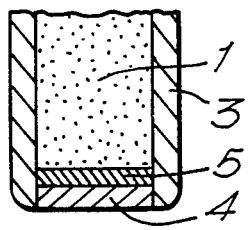
Figure 3:
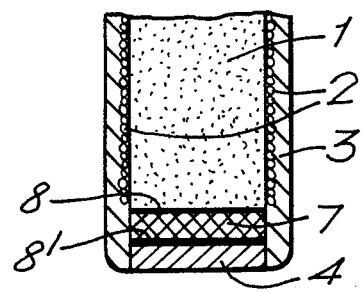

FIGS. 1 to 3 of the accompanying drawings show three particular embodiments of electrodes according to the present invention. These embodiments are in no way limiting of the scope of the invention, and are purely for illustration.

FIGS. 1 a, b and c illustrate electromagnetic electrodes in vertical cross-section, each comprising a generally rod-shaped core 1 (e.g. of mild steel) within electrical windings 2, the whole being covered on its curved surface by an insulating layer 3 (e.g. of epoxy resin or a polyolefin such as polytetrafluoroethylene). The core is terminally capped or tipped with an electrode surface 4 (e.g. of gold or graphite), optionally with a layer 5 of conductive adhesive material (e.g. silver loaded epoxy resin) interposed therebetween. In FIG. 1c the further optional features of an insulating layer 3' (e.g. of polyolefin) between the core and the electrical windings, and a surround 6 (e.g. of epoxy resin) to the electrode surface 4 to leave the surface exposed for use, are also shown.

FIG. 2 illustrates an embodiment analogous to FIG. 1a wherein the core is a permanent magnet.

In the embodiments shown in FIGS. 1 a, b and c, and 2, it is sometimes found in practice that, in assays employing labelled reagents (e.g. enzyme-labelled reagents) with a free electron-transfer mediator to aid the transfer of electrons to or from the electrode, the sensitivity of the assay may be impaired by saturation of the working electrode surface with the magnetic support (e.g. in the form of particles or beads), so preventing access by the mediator molecules and conseqently reducing the signal intensity. FIG. 3 illustrates and alternative embodiment designed to overcome this problem. In this embodiment, the working electrode surface 4 is magnetically screened from the core 1 by a screening layer 7 (e.g. of mu metal), the said screening layer and electrode surface being adhesively retained in place by conductive sandwiching layers 8,8' (e.g. of silver epoxy resin). In the embodiment shown in FIG. 3, the active surface of the electrode is, in use, maintained free of magnetic particles while allowing magnetic particles to be attracted to the side of the electrode.

FIG. 10 illustrates (not to scale) a permanently magnetic electrode in longitudinal section wherein a permanent magnet 15 (e.g. an Alnico bar magnet) is present between the core 1 and the working surface 4, the components being retained in place by adhesive layers 16, 16' (e.g. of silver loaded epoxy resin). Such an electrode may be used where it is desired to effect the separation step using the working electrode; this may give rise to a simplified assay technique, in that the use of magnetic separating means independent of the working electrode may be avoided.

As stated above, by enabling a labelled component to be magnetically held near the electrode, the sensitivity of the assay may be improved. We have demonstrated this effect by comparing the electrochemical responses of the following systems at an electromagnetic working electrode using DC cyclic voltammetry:

(a) an aqueous solution of ferrocene monocarboxylic acid (FMCA) only (electron-transfer mediator);
(b) an aqueous solution of FMCA together with magnetic particles carrying the enzyme glucose oxidase (with glucose, the substrate, in solution), with the electromagnet turned OFF;
(c) as system (b), but with the electromagnet turned ON.

The magnetic particles were prepared by covalently coupling glucose oxidase to colloidal magnetic particles of the type described in our copending British Patent Application No. 8500092, using 25% glutaraldehyde.

The electrode of Example 1 was used as the working electrode. In all three systems a supporting electrolyte of 50 mM Tris/HCl buffer (pH 7.4) was used, the FMCA concentration being constant at 0.2 mM. The assay temperature was 30° C.±1° C., and a platinum counter and a calomel reference electrode were used in conjunction with the working electrode. In systems (b) and (c) the glucose concentration was 0.1M.

Measurements were taken by DC cyclic voltammetry (which employs an unstirred system in which the observed current is limited by diffusion of the mediator) at a voltage scan rate of 2 mVs$^{-1}$.

The observed currents for each system are given in Table I.

TABLE I

| System | Current (μA) (with standard deviation) |
|---|---|
| (a) | 1.18 |
| (b) | 1.36 (±0.04) |
| (c) | 5.69 (±1.5) |

As can be seen, the current is significantly greater when the magnetic particles are held at the electrode (system c) than when they are distributed throughout the vessel (system b).

As a further demonstration of the effect of magnetically holding a labelled component near the electrode we prepared magnetic beads carrying FMCA as a redox centre, and compared the cyclic voltammograms of the beads with the electromagnet in the electrode first OFF and then ON.

The beads were prepared as follows (NB to prevent the beads sticking to the glassware, all glassware was washed with concentrated nitric acid and then water and, after drying, with a 5% solution of dichlorodimethylsilane in chloroform, then rinsed with water):

0.25 ml of magnogel beads (LKB Chemicals Ltd) was washed with 10 ml of 0.5M potassium chloride rinsed with deionised water. The gel was then introduced into a flask containing 0.15 mmoles N-ethoxycarbonyl-2-ethoxy-1,2-dihydroquinone (EEDQ, Aldrich Chemical Co) in 2 ml ethanol. 0.15 mmoles of sublimation-purified FMCA dissolved in 2 ml ethanol was added, and the mixture agitated overnight at room temperature. The gel was recovered and washed sequentially with 5% ethanol, 10 ml 1M potassium chloride and deionised water. The gel was stored in phosphate/perchlorate buffer (pH 7) before use.

Figure 4:
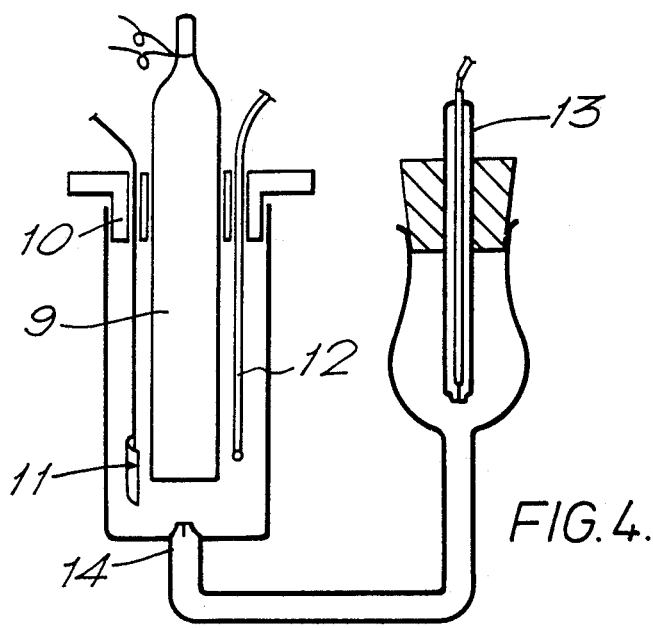

Electrochemical measurements were taken by DC cyclic voltammetry in the three-electrode cell shown in FIG. 4 of the accompanying drawings. The working electrode 9 was the electrode of Example 2, which was sealed into the cell by means of a Teflon cap 10 which cap also retained a platinum counter electrode 11 and a cannula 12. A calomel reference electrode 13 was connected to the cell by means of a luggin capillary 14. A supporting electrolyte of 0.1M NaClO$_4$/0.02M H$_3$PO$_4$ buffer (pH 7) wa used.

Figure 5:
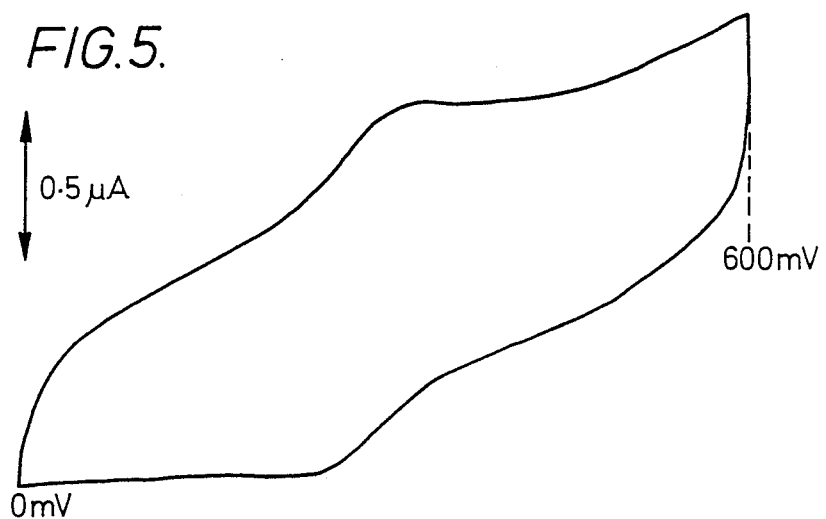

Five current/voltage cycles were performed on the beads carrying FMCA at a scan rate of 20 mVs$^{-1}$ in which the magnetic field was switched OFF and ON in alternate cycles. The DC CV trace shown in FIG. 5 of the accompanying drawings was obtained, which is identical to a trace of FMCA in solution, thus showing that coupling to the beads does not affect the electrochemistry of FMCA.

Figure 6:
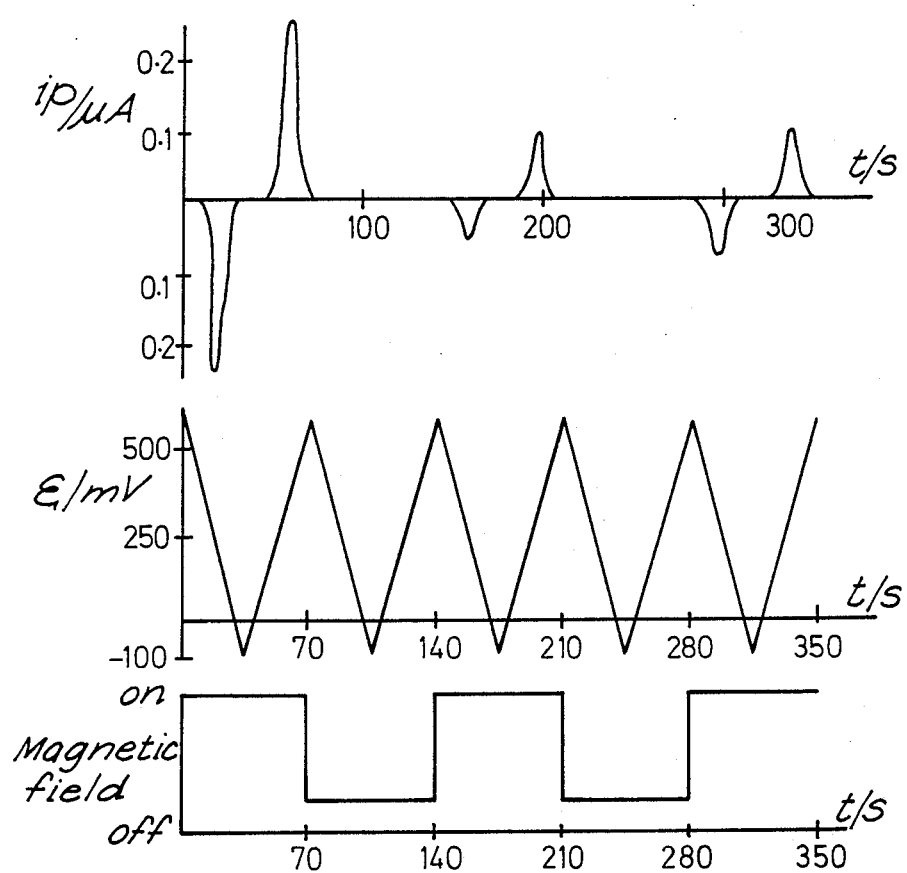

When the electromagnet in the electrode is OFF, no peaks are observed on the cyclic voltammetry trace. When the electromagnet is ON, and the beads are attracted to the electrode surface, the cyclic voltammetry trace shows anodic and cathodic peak currents (FIG. 6 of the accompanying drawings illustrates the plot of DC CV peak current vs. time obtained over 5 potential cycles, the magnetic field off on alternate cycles).

Clearly the presence of the field controls the electrochemistry—without the field, there is no electroactive species at the electrode surface and no response. The ferrocene is immobilised on the gel beads and is not in solution. That the peak current diminishes each time the gel is returned to the electrode, suggests that the orientation of gel beads en masse on the electrode surface may play some part in determining the response.

All the magnetic electrodes described above are novel, and they, and the methods of fabricating them, constitute further features of the present invention.

Thus, in a further aspect, the invention provides an electrode comprising an elongate magnetic or magnetisable core terminally capped or tipped with an electrode surface.

In a still further aspect, the invention provides an electrode as hereinbefore defined wherein the electrode surface is magnetically screened from the core.

In a still further aspect, the invention provides kits of reagents and/or apparatus for carrying out an assay of the invention. Suitable kits may comprise an electrochemical apparatus containing a magnetic working electrode, an auxiliary electrode and optionally a reference electrode, and an aqueous assay medium with suitable components present, including a labelled component which may or may not be immobilised on a magnetic support (e.g. in the form of particles or beads).

Components, including the sample to be assayed, may conveniently be introduced through an entry port provided in the apparatus.

The apparatus may be automated so that components are introduced and/or removed in a predetermined sequence, with control of the incubation temperature. Advantageously the apparatus may be pre-calibrated and provided with a scale whereby the perturbation in the electrochemical characteristic of the components may be read off directly as an amount of ligand in the sample.

Examples of ligands which may be assayed by the methods of the invention are given in Table II below, together with an indication of a suitable specific binding partner in each case.

TABLE II

| Ligand | Specific Binding Partner |
|---|---|
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) |
| enzyme cofactor (substrate) | enzyme |
| lectin | specific carbohydrate |
| carbohydrate | specifc lectin |

The method of the invention has very broad applicability, but in particular may be used to assay: hormones, including peptide hormones (e.g. thyroid stimulating hormone (TSH), luteinising hormone (LH), follicle stimulating hormone, (FSH) ,human chorionic gonadotrophin (HGC), insulin and prolactin) or non-peptide hormones (e.g. steroid hormones such as cortisol, estradiol, progesterone and testosterone and thyroid hormones such as thyroxine (T4) and triiodothyronine), proteins (e.g. carcinoembryonic antigen (CEA) and alphafetoprotein (AFP)), drugs (e.g. digoxin), sugars, toxins or vitamins.

The invention will be particularly described hereinafter with reference to an antibody or an antigen as the ligand. However, the invention is not to be taken as being limited to assays of antibodies or antigens.

It will be understood that the term "antibody" used herein includes within its scope
  (a) any of the various classes or sub-classes of immunoglobulin, e.g. IgG, IgM, derived from any of the animals conventionally used, e.g. sheep, rabbits, goats or mice,
  (b) monoclonal antibodies,
  (c) intact molecules or "fragments" of antibodies, monoclonal or polyclonal, the fragments being those which contain the binding region of the antibody, i.e. fragments devoid of the Fc portion (e.g., Fab, Fab', F(ab')2) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacteria fragments, cells, cell fragments and viruses) and haptens which may be rendered antigenic under suitable conditions.

A labelled antibody or antigen reagent immobilised onto a magnetic support (e.g. in the form of particles or beads) may be prepared in, for example, any of the following ways:
  (1) labelling free reagent and subseqently immobilising the reagent onto the support at a site remote from the label by bonding interactions between functional groups of the antibody or antigen molecule and the support, or by cross-linking or adsorption onto the surface of the support. Such methods for immobilising antibodies or antigens are known, for example, as described in European Patent Application No. 83305834.0 (publication number 105,714);
  (2) incorporating a label into the molecular structure of a pre-immobilised reagent;
  (3) incorporating a bifunctional label into the molecular structure of free antibody or antigen so as to enable one function to interact with the support;
  (4) immobilising a bifunctional label onto the support, so as to enable one function to interact with the molecular structure of free antibody or antigen; and
  (5) immobilising an unlabelled antigen or antibody onto the support and subseqently complexing to the antigen or antibody a labelled antibody or antigen respectively.

Labelling of reagents may, for example, be effected by conventional methods.

The invention also includes within its scope "linked" assays in which a labelled antibody or antigen reagent is bound to the magnetic support via one or more linking species. Suitable "linked" assay systems are illustrated by way of examples as follows:

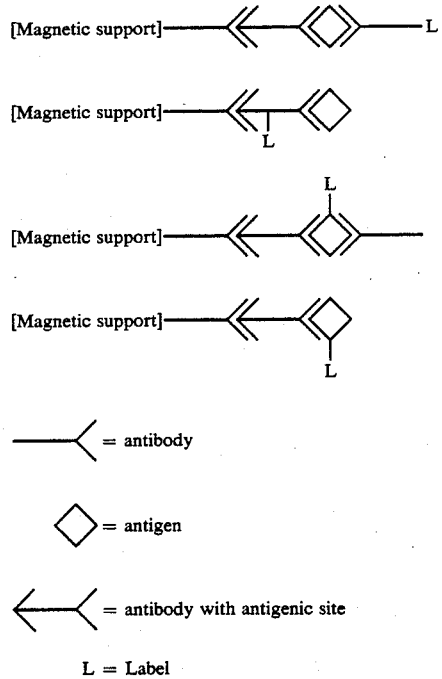

If the antigen is multideterminant, "linked sandwich" antibody or antigen assays are achievable.

Thus, for example, antigens or antibodies may be assayed by homogeneous or heterogeneous competitive, direct, linked competitive, linked direct, sandwich or linked sandwich techniques according to the invention. Sandwich assays may take the form of forward, reverse or simultaneous sandwich assays.

In the preferred methods of the invention, the use of a magnetic electrode together with reagents immobilised on a magnetic support enables easy separation of bound from free immunoreagents and enables the electrochemical species of interest to be held in close proximity to the electrode surface.

The magnetic electrode can fulfil a number of roles in such an assay. It supplies a surface at which the electrochemistry of the label is measured but can also achieve a separation step in one of two ways:

(a) by trapping a layer of particles over its surface by means of the magnetic field, the bound and free label in the system may be effectively separated permitting the electrochemical effects of the bound label to occur as the bound label is held against the electrode surface. The approach of free label to the electrode surface is limited due to the presence of the magnetic particles and therefore its electrochemical contribution is diminished, or (b) the electrode can permit separation of bound from free label, the bound label being readily transferred to an electrochemical cell if necessary where the magnetic field is broken (e.g. by turning off the electric current) and the electrochemistry of the label can then be studied at an electrode surface which is free from magnetic particles etc. This system may be beneficial for enzyme assays as the electrochemistry of oxidoreductase enzymes requires the diffusion of substrate to, product from, and mediator to and from the enzyme and diffusion of the mediator to and from the electrode surface. Thus more sensitive enzyme assays may result if the electrode is used to effect separation.

(When antibodies are coupled to magnetic particles there is no control over the number of antibody molecules coupled to each magnetic particle, neither is there any control of the orientation of said antibody molecules over the particle surface. Thus when the magnetic particle is attracted to the electrode the number of electrochemically active molecules at the electrode surface will depend on the immune reaction and random orientation of the magnetic particle).

By way of example only, the invention includes inter alia the following embodiments:

ⓜ = magnetic support (e.g. particles or beads)
L = label
←⊰ = antibody with antigenic site
? indicates species under assay
∪ = magnetic electrode
—⊰ = antibody
◇ = antigen

HOMOGENEOUS ASSAYS

1. Direct antigen assay

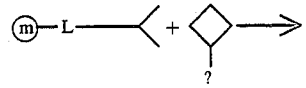

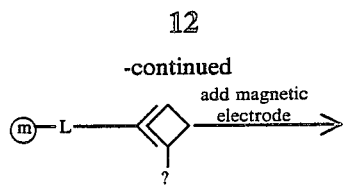

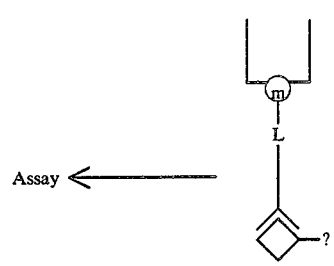

The binding of antigen to antibody perturbs the electrochemistry of the label. If the label L is an oxidoreductase enzyme (e.g. glucose oxidase, GOD), the appropriate substrates and mediators of the enzyme must be added before the assay can be quantified.

2. Competitive antigen assay

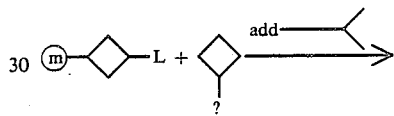

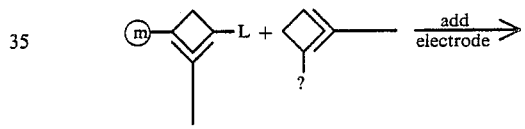

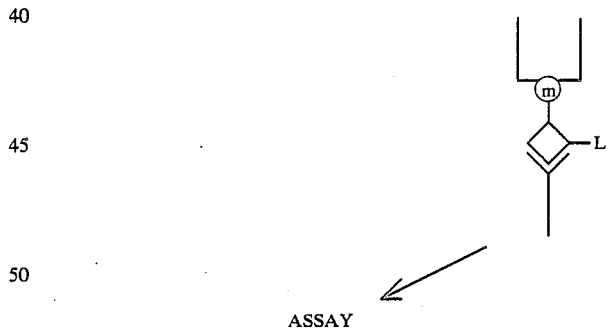

The direct competition between ligand and labelled ligand analogue coupled to the magnetic solid phase for specific binding partner permits the assay to be made. Binding of antibody to labelled antigen perturbs the electrochemistry of the label.

3. Direct antibody assay p

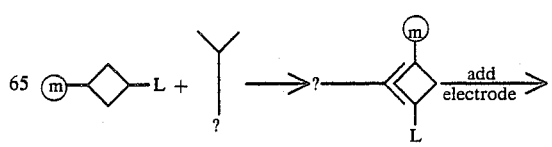

-continued

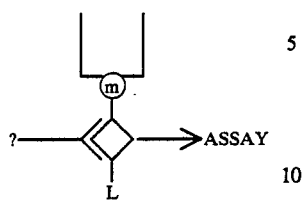

The decrease in signal is a direct quantitative measure of the antibody being assayed.

4. Sandwich antibody assay

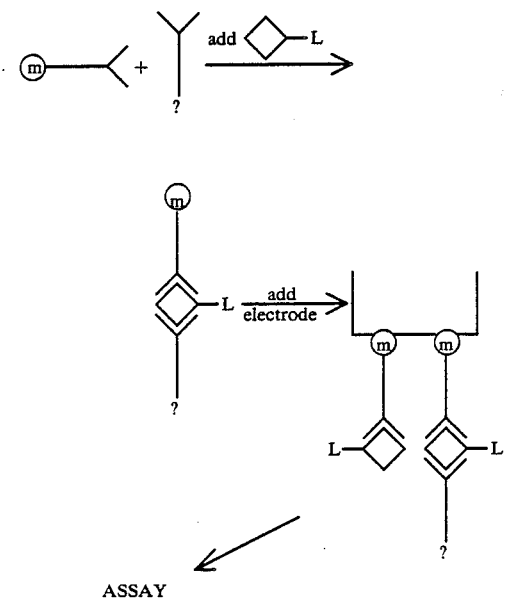

ASSAY

The amount of label present at the electrode is a measure of the unknown antibody concentration.

5. Linked antibody assay

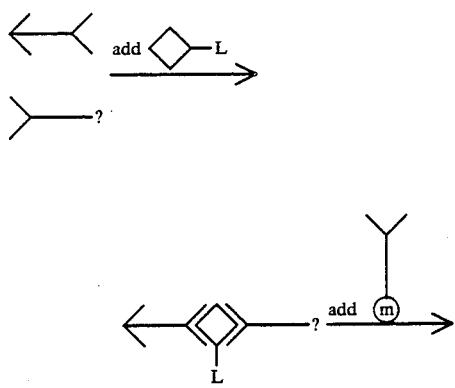

-continued

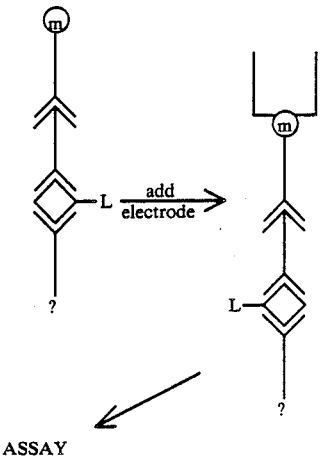

ASSAY

The amount of label assayed directly relates to the amount of unknown antibody present as binding of the unknown antibody to the labeled antigen perturbs the label's electrochemistry.

6. Competitive antibody assay

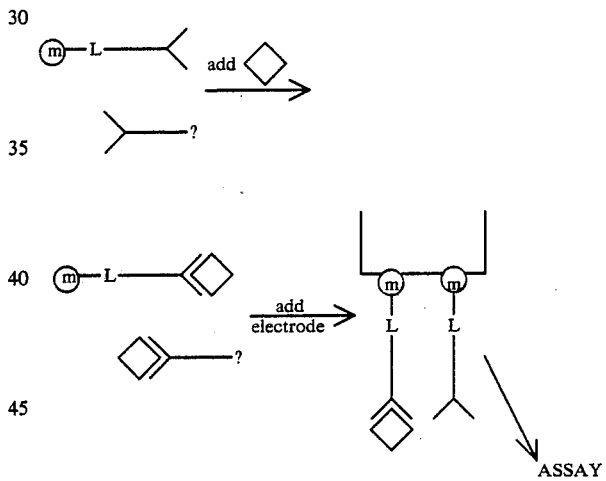

ASSAY

In this assay the degree of perturbation of the electrochemical characteristics of the label on antigen/antibody binding permits antibody quantification.

HETEROGENEOUS ASSAYS

7. Sandwich antigen assay

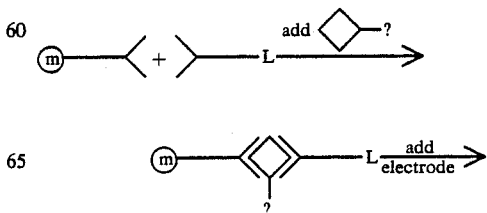

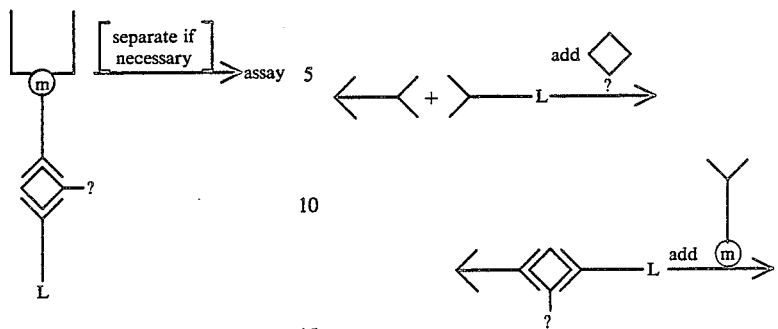

The antigen concentration relates directly to the amount of label present at the electrode.

8. Competitive Antigen Assay

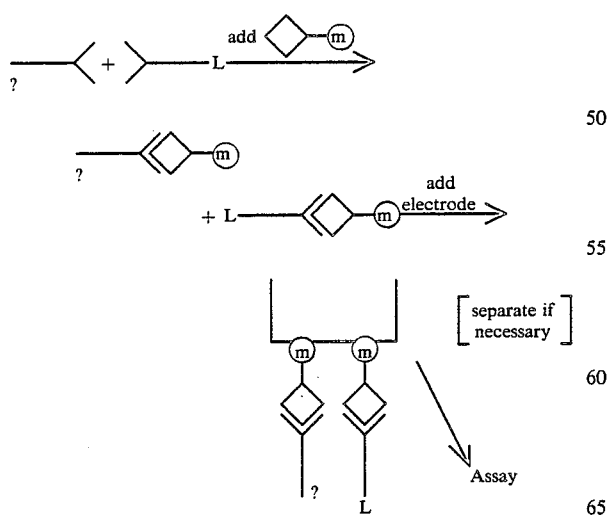

The direct competition between ligand and labelled ligand analogue for specific binding partner permits the assay to be made.

9. Competitive antibody assay

In this assay the amount of label present at the electrode is a measure of antibody concentration.

10. Linked sandwich antigen assay

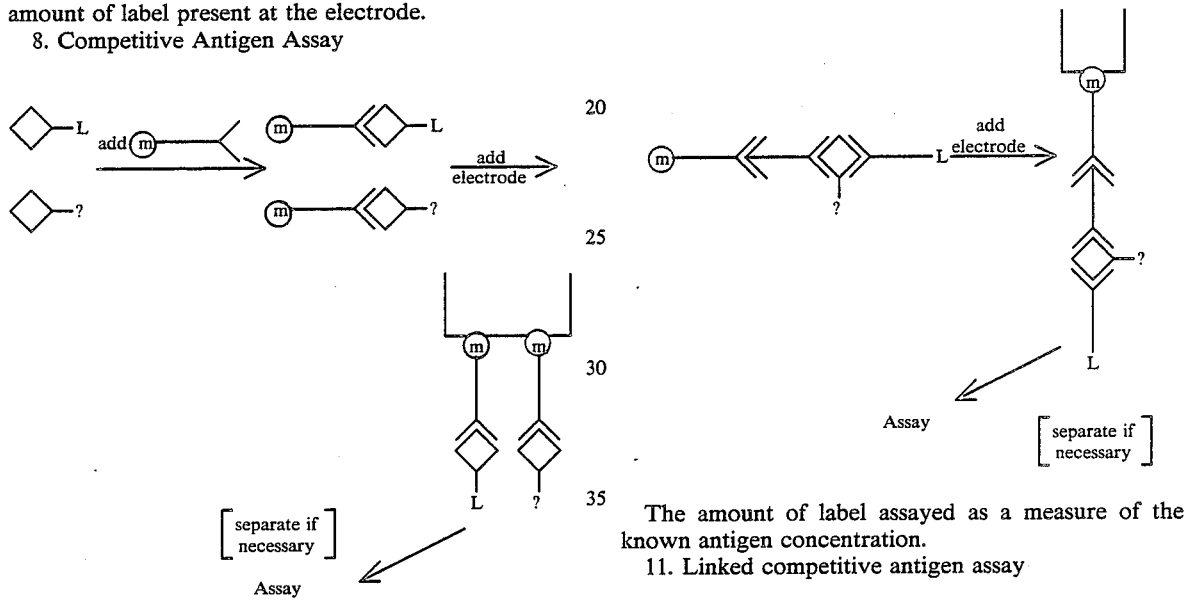

The amount of label assayed as a measure of the known antigen concentration.

11. Linked competitive antigen assay

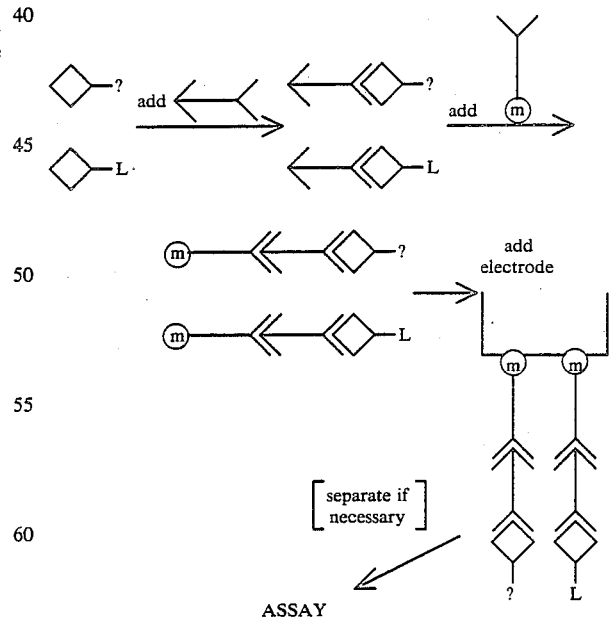

The amount of label assayed is a measure of the unknown antigen concentration.

The following non-limiting Examples are included as further illustration of the present invention:

EXAMPLE 1

Electromagnetic Electrode

An electromagnetic electrode of the type illustrated in FIG. 1b was fabricated by wrapping two turns of 0.1 mm diameter insulated copper wire round a steel rod 10 cm long×3 mm diameter. The rod was tipped with a graphite disc (4 mm diameter) using silver loaded epoxy resin as an adhesive, and encased in epoxy resin.

EXAMPLE 2

Electromagnetic Electrode

An electromagnetic electrode of the type illustrated in FIG. 1c was fabricated by fitting a 9 cm length of heat-shrink polyolefin tubing over a rod of mild steel (11 cm long×3.5 mm diameter) which had previously been capped with spun gold. No adhesive layer was employed between the mild steel rod and the gold cap. Six layers of 0.315 mm diameter copper wire were then wound over this core to a resistance of 30Ω, the windings sealed in by a second length of heat-shrink polyolefin tubing to give total diameter of the electrode of 10.5 mm. The electrode was completed by setting the working end of the electrode in epoxy resin, leaving only the gold working surface exposed.

EXAMPLE 3

Assay of Human Chorionic Gonadotrophin (hcG) Using an Enzyme Modified Antibody with Enhancement or Perturbation Using Controlled External Influences In this Example, an enzyme labelled antibody reagent is employed in a "linked" assay system using FMCA as an electron-transfer mediator. The antibody with antigenic site is anti-hCG conjugated to fluorescein isothiocyanate (FITC) and the immobilised antibody is anti-FITC covalently coupled to magnetisable solid phase.

The perturbation in the electrochemical characteristic, from which the assay is calculated, is enhanced (after separation of the bound and free components) by magnetically holding at least a portion of the labelled component in the vicinity of the working electrode.

Preparation of Starting Materials (i) Enzyme modified anti-hCG monoclonal antibodies Monoclonal antibodies were obtained from mouse ascites fluid by the process reported by Galfre and Milstein in Methods of Enzymology 73, 3 (1981). Antibodies from individual hybridoma cell lines were screened to identify those producing antibody to discrete antigenic determinants. Those having the highest affinities to hCG were selected for use in the assay.

To 6 mg of antibody A (in 2 ml of sodium phosphate buffer, 100 mM pH 7.4) 200 μl of 8-mercaptoethylamine (100 mM) and ethylenediaminetetraacetic acid, disodium salt (10 mM) in water, were added. The mixture was incubated at 37° C. for 90 minutes and the antibody was desalted on a gel filtration column (TSK 3000 SW) preequilibrated in phosphate buffer.

14 mg of glucose oxidase was dissolved in 1.3 ml of phosphate buffer to which 20 μl of a 15 mg solution of succinimidyl 4-(N-maleimide-methyl) cyclohexane-1-carboxylate (SMCC) in dioxan was added whilst stirring. 20 μl aliquots of SMCC were added at 5 minute intervals until a total of 180 μl of SMCC in dioxan was added and, after the reaction had been allowed to proceed at 30° C. for two hours, the solution was desalted on a gel filtration column (G-25) preequilibrated in phosphate buffer (100 mM, pH 7.0 containing 100 mM EDTA).

Equimolar ratios of enzyme and antibody were mixed and rolled at 4° C. under argon for 68 hours. The enzyme/antibody conjugate was then purified by gel filtration yielding a product incorporating 1 enzyme molecule per antibody molecule. The fractions which showed both high enzyme and immunological activities were retained and used in the assay.

(ii) Preparation of anti-hCG (antibody B) conjugated to fluorescein isothiocyanate (FITC)

A second monoclonal antibody to hCG (antibody B) specific for a different antigenic determinant was conjugated to FITC.

Conjugation of FITC to monoclonal antibody was achieved by reacting 200 μg fluorescein isothiocyanate (FITC) Sigma London Chemical Co., England with 5 mg antibody in 1.4 ml sodium bicarbonate buffer, 0.2M, pH 9.0, for 18 hours at room temperature. The reaction mixture was purified by gel filtration on Sephadex G-50 superfine, giving a product incorporating an average of 6 molecules FITC per antibody molecule.

(iii) Preparation of anti-FITC antibody covalently coupled to magnetisable solid phase Anti-FITC was a conventional polyclonal antiserum obtained by immunising sheep with FITC conjugated to keyhole limpet haemocyanin. The magnetisable cellulose particles were a composite of cellulose containing approximately 50% black ferric(ous) oxide ($Fe_3O_4$), with mean particle diameter of 3 microns (see Forrest and Rattle, "Magnetic Particle Radioimmunoassay" in Immunoassays for Clinical Chemistry, p 147–162, Ed Hunter and Corrie, Churchill Livingstone, Edinburgh (1983)). Anti-FITC antiserum was covalently coupled to the magnetisable cellulose following cyanogen bromide activation of the cellulose, according to the procedure of Axen et al, Nature 214, 1302–1304 (1967). The antiserum was coupled at a ratio of 2 ml antiserum to 1 gram of magnetisable solid phase.

Anti-FITC magnetisable solid phase was diluted to 10 mg per ml in Tris-HCl buffer (10 mM per liter, pH 7.4).

(iv) Preparation of hCG standard solutions

A freeze dried preparation of hCG, calibrated against the first international reference preparation (75/537) was obtained from Biodata SpA, Milan, Italy. This sample was diluted in buffer (Tris-HCl, (10 mM, pH 7.4) to the desired concentration.

(v) Apparatus used for electrochemical measurement

Cyclic voltammetry was performed in a three electrode electrochemical cell using a pyrolytic working electrode. The Apparatus was the same as that shown in vertical cross-section in FIGS. 7(a) and 7(b) of the accompanying drawings. The working electrode 1 was composed of an elongate core 2 of steel tipped with a working surface 3 of pyrolytic graphite and having a coating 4 of epoxy resin. The auxiliary (counter) electrode 5 was of platinum. A calomel reference electrode 6 was used, connected to the cell via a luggin capillary 7. The cell and reference electrode were enclosed in a water jacket 8. FIG. 7(b) illustrates schematically the circuit employed for cyclic voltammetry. In this Figure, C represents the auxiliary (counter) electrode, W the working electrode and R the reference electrode. The electrochemical current i was measured using a potentiostat.

(vi) Assay procedure for hCG

An immunometric immunoassay using glucose oxidase modified anti-hCG monoclonal antibody was used to measure hCG.

Duplicate samples were run in which 50 μl of hCG standard was mixed with 50 μl antibody A (9.4 μg protein per ml) and 50 μl of antibody B 6 μg protein per ml). After mixing, the samples were incubated at room temperature for 30 minutes, 100 μl of anti-FITC magnetisable solid phase was added and, after vigorous mixing, was incubated for 5 minutes, also at room temperature. The application of an external magnetic field permitted the separation of bound and free components, the solid phase being retained and the supernatant discarded. After two washes with 250 μl of distilled water the solid phase was resuspended in buffer (100 μl of 10 mM Tris/HCl, pH 7.4) and added to the electrochemical cell which contained electron transfer mediator (40 μl of ferrocene monocarboxylic acid (FMCA) 6.7 mM in 10 mM Tris/HCl, pH 7.4), enzyme substrate (40 μl of molar glucose solution containing 100 mM magnesium chloride) and 170 μl of Tris/HCl buffer (10 mM, pH 7.4). The application of an external magnetic field to the working electrode by contacting it with a permanent magnet caused the magnetic solid phase to be concentrated on the electrode surface. Once the solid phase had been concentrated at the working electrode surface and reached thermal equilibrium (temperature $T=37 \geq \pm 1°$ C.), the electrochemical current due to the bound glucose oxidase activity was measured by making a cyclic voltammogram from +120 mV to +420 mV versus a standard calomel electrode (voltage scan rate=2 mV per second).

Figure 8:
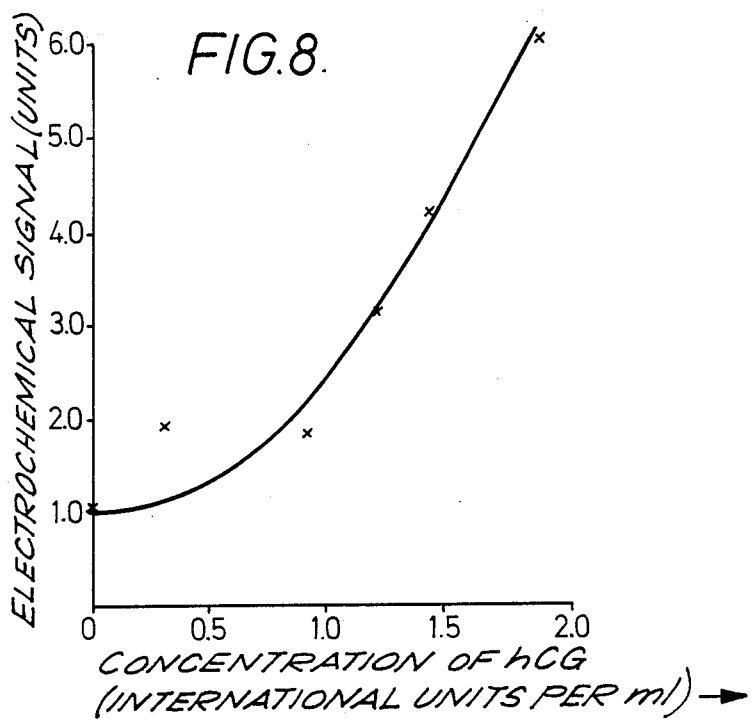

A plot of electrochemical signal versus hCG concentration is shown in FIG. 8. The electrochemical signal is defined as $$\text{signal} = \frac{\text{peak current for sample} - \text{peak } FMCA \text{ background current}}{\text{peak current for zero} - \text{peak } FMCA \text{ background current}}$$

The electrochemical signal (in arbitrary units) is plotted on the vertical axis whilst the hCG concentration (in International units per millilitre) is plotted on the horizontal axis.

EXAMPLE 4

Assay of Human Chorionic Gonadotrophin (hCG) Using an Enzyme Modified Antibody With Enhancement of Perturbation Using Controlled External Influences This Example is similar in nature to Example 3, but employs dimethylaminomethyl ferrocene as electron transfer mediator and uses an alternative definition of the electrochemical signal from which the assay is determined.

Preparation of Starting Materials (i) Enzyme modified anti-hCG monoclonal antibodies:
The method was the same as that in Example 3.

(ii) Preparation of anti-hCG (antibody B) conjugated to fluorescein isothiocyanate (FITC):
The method employed was the same as that in Example 3.

(iii) Preparation of anti-FITC antibody covalently coupled to magnetisable solid phase:
For method see Example 3.

(iv) Preparation of hCG standard solutions:
The method was the same as that in Example 3.

(v) Apparatus used for electrochemical measurement:
The electrochemical apparatus was the same equipment as that of Example 3.

Assay Procedure for hCG

An immunometric immunoassay using glucose oxidase modified anti-hCG monoclonal antibody was used to measure hCG.

Duplicate samples were run in which 50 μl of hCG standard was mixed with 50 μl antibody A (10 μg protein per ml) and 50 μl of antibody B (6 μg protein per ml). After mixing, the samples were incubated at room temperature for 30 minutes. 100 μl of anti-FITC was added and, after vigorous mixing, was incubated for 5 minutes, also at room temperature. The application of an external magnetic field permitted the separation of bound and free components, the solid phase being retained and the supernatant discarded. The retained solid phase was washed three times with 200 μl of 10 mM Tris/HCl buffer, pH 7.4 containing 0.9% w/v sodium chloride before being resuspended in 100 μl 10 mM Tris/HCl buffer, pH 7.4. The solid phase was transferred to the electrochemical cell which contained electron transfer mediator (40 μl of dimethylaminomethyl ferrocene 0.6 mM in 10 mM Tris/HCl, pH 7.4), enzyme substrate (40 ul of molar glucose containing 100 mM magnesium chloride) and 170 μl of Tris/HCl buffer (10 mM pH 7.4). The application of an external magnetic field to the working electrode by contacting it with a permanent magnet caused the magnetic solid phase to be concentrated on the electrode surface. Once the solid phase had been concentrated at the electrode surface and reached thermal equilibrium (assay temperature=$37° \pm 1°$ C.), the electrochemical current due to the bound glucose oxidase activity was measured by making a cyclic voltammogram from 0 to +500 mV versus a standard calomel electrode (voltage scan rate=5 mVs$^{-1}$).

Figure 9:
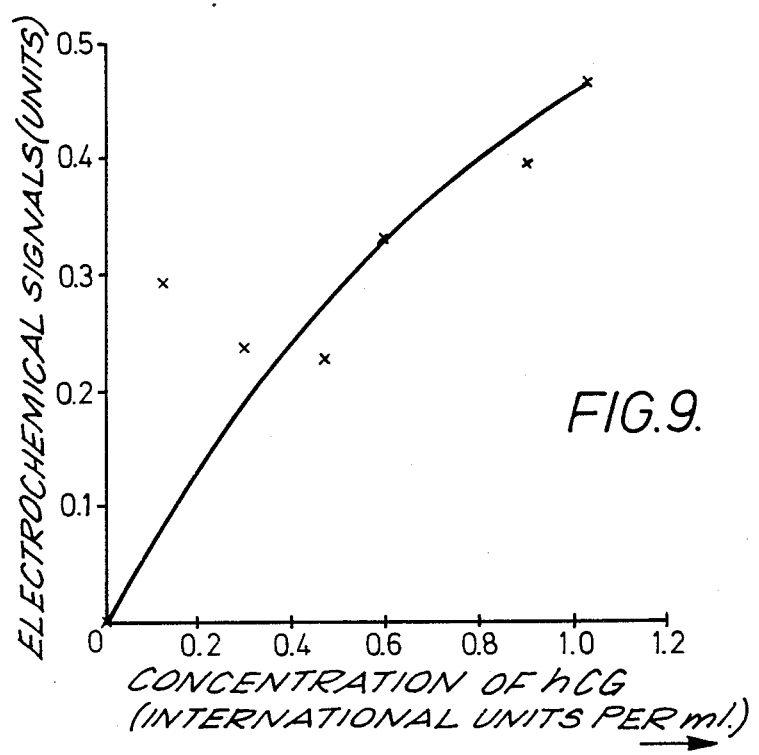

A plot of electrochemical signal versus hCG concentration is shown in FIG. 9. The electrochemical signal is defined as $$\text{signal} = \frac{i - i_o}{i_o}$$

where
i = peak current for sample − peak mediator current
$i_o$ = peak current for zero sample − peak mediator current The electrochemical signal (in arbitrary units) is plotted on the vertical axis whilst hCG concentration (in International Units per millilitre) is plotted along the horizontal axis.

EXAMPLE 5

Assay of Human Chorionic Gonadotrophin (hCG) Using an Enzyme Modified Antibody with Enhancement of Pertubation Using Controlled External Influences This example is similar in nature to Example 4 but employs an electrode which incorporates a permanent magnet in its structure. The assay is separated and measure directly using this electrode.

Construction of the Magnetic Working Electrode.

A magnetic electrode of the type illustrated in FIG. 10 was fabricated by fitting a 9 cm length of heat-shrink polyolefin tubing over a rod of mild steel (11 cm long×3.5 mm diameter) which had previously been capped with a disc of pyrolytic graphite (1 mm thick×4 mm diameter) attached to an Alnico permanent magnet (1 cm long×4 mm diameter). Silver loaded epoxy resin was used to attach the pyrolytic graphite to the magnet and to attach the magnet to the steel rod.

Preparation of the Starting Materials (i) Enzyme modified monoclonal antibodies (antibody A):
The method was the same as that in Example 3.
(ii) Preparation of anti-hCG (Antibody B) conjugated to fluorescein isothiocyanate (FITC):
The method was the same as that in Example 3.
(iii) Preparation of anti-FITC antibody covalently coupled to maqnetisable solid phase:
The method was the same as that in Example 3.
(iv) Preparation of hCG standard solutions:
The method was the same as that in Example 3.
(v) Apparatus used for electrochemical measurement:
The electrochemical apparatus was the same as for Example 3.

Assay Procedure for hCG

An immunometric immunoassay using glucose oxidase modified anti-hCG monoclonal antibody was used to measure hCG.

Duplicate samples were run in which 25 μl of hCG standard was mixed with 50 μl of antibody A (10.0 μg protein per ml) and 50 μl of antibody B (6 μg protein per ml) in the electrochemical cell (temperature=37°±0.5° C.). After mixing, the samples were incubated at 37° C. for 15 minutes. 100 μl of anti-FITC was added and, after vigorous mixing, was incubated for 5 minutes, also at 37° C. 40 μl of electron transfer mediator (dimethylaminomethyl ferrocene, 0.3 mM in 10 mM Tris/HCl, pH 7.4); 40 μl of enzyme substrate (molar glucose containing 100 mM magnesium chloride) and 95 μl of Tris/HCl buffer (10 mM pH 7.4) were added to the cell which caused the magnetisable solid phase to be concentrated at the surface of the electrode. Once the solid phase had been localised at the electrode surface and thermal equilibrium had been reached (temperature=37°±0.5° C.), the electrochemical current due to the bound glucose oxidase activity was measured by making a cyclic voltammogram from 0 to 500 mV versus a standard calomel electrode (voltage scan rate=5 mVs$^{-1}$).

Figure 11:
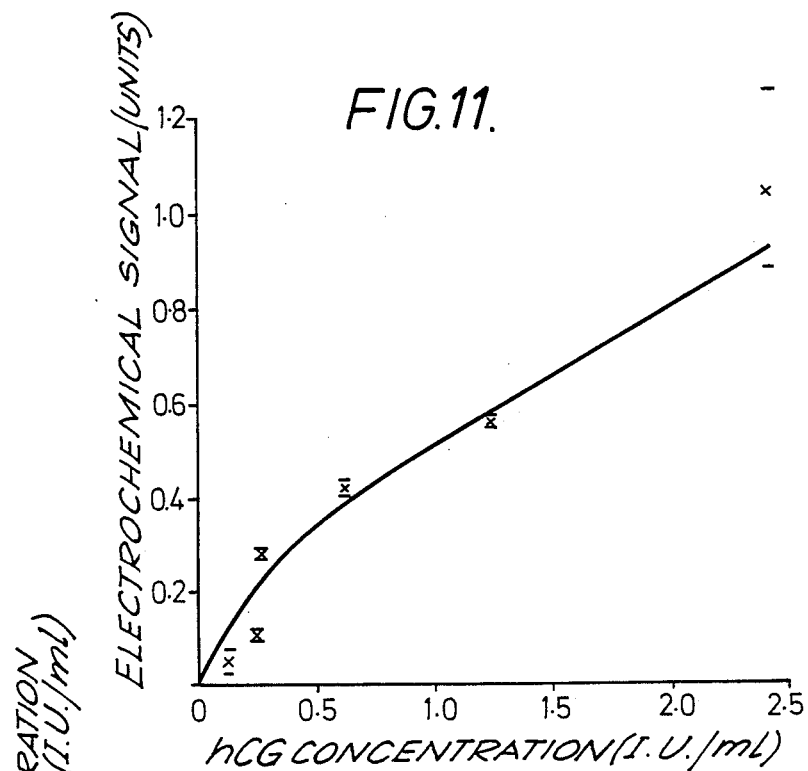

A plot of electrochemical signals versus hCG concentration (solid phase concentrated at the electrode surface) is shown in FIG. 11. The electrochemical signal is defined as in Example 4 and is plotted (in arbitrary units) on the vertical axis whilst hCG concentration (in International Units per milliliter) is plotted along the horizontal axis.

This method of assay was further used to measure the hCG concentration in urine samples obtained from pregnant women. The assay methodology was the same except that 25 μl of urine was substituted for 25 μl of hCG in buffer. The data obtained were compared with data obtained on the same samples using a commercial immunoradiometric hCG assay kit (IRMA) (hCG MAIACLONE code number 12304, supplied by Serono Diagnostics Ltd., 21 Woking Business Park, Albert Drive, Woking, Surrey GU21 5JY, U.K.). The instructions for assay supplied with the IRMA kit were adhered to in these measurements.

Figure 12:
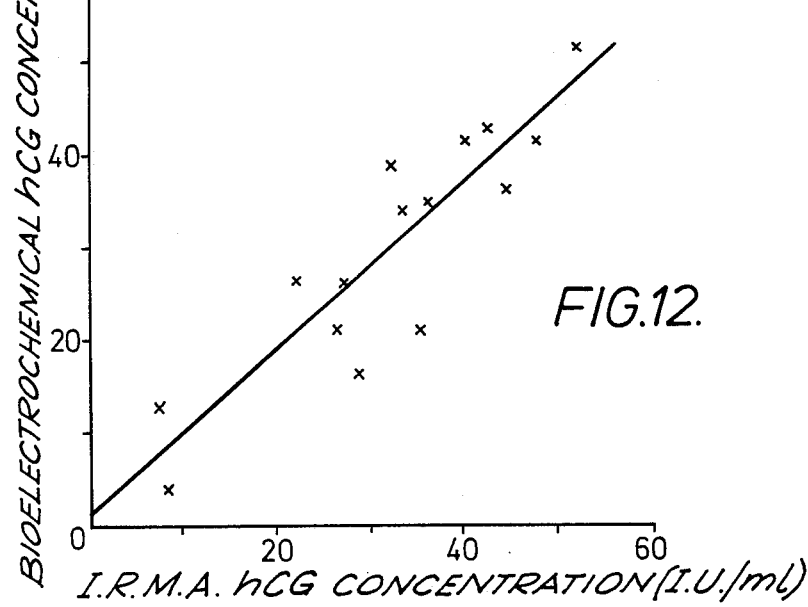

The results of the electrochemical assay of urinary hCG are compared with those obtained with the IRMA assay in FIG. 12. The electrochemical hCG concentrations (in International Units per milliliter) are plotted on the vertical (y) axis whilst the IRMA assay concentrations (also in International Units per milliliter) are plotted along the horizontal (x) axis. Linear regression analysis of the data produced the following equation for the straight line:

$$y = 0.042 + 0.936\, x$$

where
y=electrochemical hCG concentration
x=IRMA hCG concentration.

We claim:

1. A method of effecting an electrochemical specific-binding assay of a ligand, either qualitatively or quantitatively, in an apparatus comprising at least one electrode, in which method a labelled component of the assay medium is, at least in part, magnetically held in the vicinity of the electrode.

2. A method as claimed in claim 1 which includes a separation step, whereby bound label may be separated from free label in the assay medium.

3. A method as claimed in claim 1 which includes the step of determining a perturbation in an electrochemical characteristic of components of the assay medium associated with a ligand complexing reaction.

4. A method as claimed in claim 1 wherein a redox centre label, an enzyme label in the presence of an electron-transfer mediator or an electron-transfer mediator label in the presence of an electron donor or acceptor is employed.

5. A method as claimed in claim 4 wherein ferrocene or a derivative thereof is employed.

6. A method as claimed in claim 1, wherein the labelled component of the assay medium is retained in the vicinity of the working electrode by immobilising at least some of the labelled component on a magnetic support and employing a magnetic working electrode.

7. A method as claimed in claim 1 wherein the ligand is an antibody or antigen.

8. A method as claimed in claim 2, wherein a redox center label, an enzyme label in the presence of an electron-transfer mediator or an electron-transfer mediator label in the presence of an electron donor or acceptor is employed.

9. A method as claimed in claim 3, wherein a redox center label, an enzyme label in the presence of an electron-transfer mediator or an electron-transfer mediator label in the presence of an electron donor or acceptor is employed.

10. A method as claimed in claim 2, wherein the labelled component of the assay medium is retained in the vicinity of the working electrode by immobilising at least some of the labelled component on a magnetic support and employing a magnetic working electrode.

11. A method as claimed in claim 3, wherein the labelled component of the assay medium is retained in the vicinity of the working electrode by immobilising at least some of the labelled component on a magnetic support and employing a magnetic working electrode.

12. A method as claimed in claim 2, wherein the ligand is an antibody or antigen.

13. A method as claimed in claim 3, wherein the ligand is an antibody or antigen.

14. A method of effecting an electrochemical specific-binding assay of a ligand, either qualitatively or quantitatively, in an apparatus comprising at least one working electrode, in which method a sample to be tested is brought in contact with the assay medium, the assay medium containing a labelled component which is, at least in part, magnetically held in the vicinity of the working electrode, an electrochemical characteristic of the components of the assay medium associated with a ligand complexing reaction is measured and whether there is, and optionally the extent to which there is, a perturbation in that electrochemical characteristic is determined.

* * * * *